United States Patent [19]

Bardasz

[11] Patent Number: 4,994,575
[45] Date of Patent: Feb. 19, 1991

[54] DIPENTENE ACRYLIC ACID IMIDAZOLINES AND THEIR USE AS CORROSION INHIBITORS

[75] Inventor: Ewa A. Bardasz, Mentor, Ohio

[73] Assignee: Union Camp Corporation, Wayne, N.J.

[21] Appl. No.: 429,232

[22] Filed: Oct. 30, 1989

[51] Int. Cl.$^5$ .......................................... C07D 233/06
[52] U.S. Cl. ..................................... 548/352; 422/12; 422/13; 422/16
[58] Field of Search ........................................ 548/352

[56] References Cited

U.S. PATENT DOCUMENTS

Re. 23,227  5/1950  Blair et al. ............................ 548/352
2,713,583  7/1955  Smith .................................... 548/352
4,634,729  1/1987  Pavlin et al. ......................... 560/128

Primary Examiner—Mary C. Lee
Assistant Examiner—Lenora Miltenberger
Attorney, Agent, or Firm—Edward J. Sites

[57] ABSTRACT

Imidazolines of the formula:

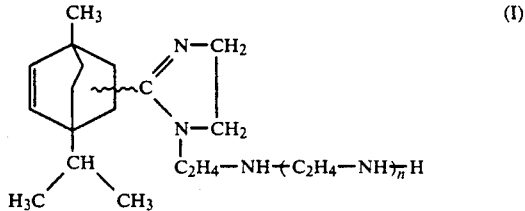

wherein n is a whole number integer of from 1 to 6, are metal corrosion inhibitors.

3 Claims, No Drawings

DIPENTENE ACRYLIC ACID IMIDAZOLINES AND THEIR USE AS CORROSION INHIBITORS

BACKGROUND OF THE INVENTION

1. Field of the Invention

The invention relates to compositions and methods for inhibiting corrosion of metals and more particularly to novel imidazolines and the process of their use as corrosion inhibitors.

2. Brief Description of the Prior Art

The prior art literature is replete with descriptions of a wide variety of methods and compositions for inhibiting the corrosion of metals, particularly ferrous metals. The massive bulk of literature on this subject over many years, is itself evidence of the lack of complete satisfaction with methods and compositions heretofore available to the artisan. The lack of full satisfaction is due to a broad variety of factors, such as cost, inefficiency of method, toxicity of compositions, relative ineffectiveness, incompatibility of compositions, and difficulty in handling.

One U.S. patent which is representative of the prior art descriptions is the U.S. Pat. No. 2,466,517 issued to Blair, Jr., et al. on Apr. 5, 1949. This patent describes a wide variety of imidazolines and their use as corrosion inhibitors. Similar disclosure is set forth in the U.S. Pat. No. RE. 23,227 (Blair, Jr., et al.).

The compounds and the process of the present invention exhibit improvements in anti-corrosion activity.

SUMMARY OF THE INVENTION

The invention comprises an imidazoline of the formula:

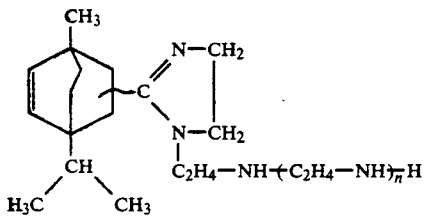

wherein n represents a whole number integer of from 1 to 6 and the wavy bond line indicates that the ring substituent group is bonded to a carbon atom at one of the 5 or 6 positions of the bicyclo moiety.

The invention also comprises anti-corrosion compositions which comprise the compounds of the invention in an oil carrier.

The invention also comprises a process of inhibiting corrosion of metals exposed to oxidative conditions, which comprises; applying to the metal a corrosion inhibiting proportion of an imidazoline of the formula (I), given above.

The compounds, compositions and process of the invention are useful to inhibit corrosion of metals, particularly rusting of ferrous metals.

DETAILED DESCRIPTION OF THE PREFERRED EMBODIMENTS OF THE INVENTION

The compounds of the formula (I) given above are imidazolines, which may be prepared by the reaction of the Diels-Alder adduct (1:1 adduct) of acrylic acid and α-terpinene with an appropriate polyalkylenepolyamine of the formula:

$$H_2N-C_2H_4-NH+C_2H_4-NH)_{\overline{m}}H \quad (II)$$

wherein m is a whole number integer of from 2 to 7. The reaction may be carried out under the conditions described, for example, in the U.S. Pat. Nos. 1,999,989 dated Apr. 30, 1935 (Bockmuhl et al.); 2,155,877 issued Apr. 25, 1939 (Waldmann et al.); and 2,155,878 issued Apr. 25, 1939 (Waldmann et al.), all of which are incorporated herein by reference thereto. The reaction is well known; see also Chemical Review, Vol. 32, 47(43).

The 1:1 Diels-Alder adduct of α-terpinene and acrylic acid, employed as starting reactants in the preparation of imidazoline compounds used in the present invention is a well known compound, as is its preparation; see for example the method described in U.S. Pat. No. 4,634,729 (Example 7) issued to Veazey and Pavlin on Jan. 6, 1987.

The polyamines (II) described above are also well known compounds, as is the method of their preparation. Representative of the polyamines of formula (II) given above are triethylenetetramine, tetraethylenepentamine, pentaethylenehexamine, hexaethyleneheptamine, heptaethyleneoctaamine, and octaethylenenonamine.

Alternatively, the imidazoline compounds (I) may be prepared by heating the corresponding carboxyamides of the formula:

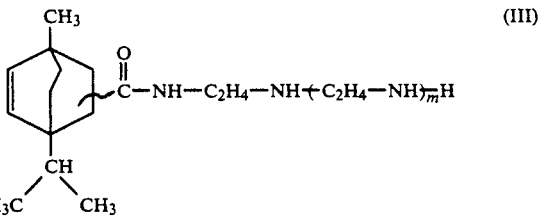

wherein m has the meaning previously ascribed to it.

Heating may be carried out to a temperature within the range of from about 50° C. to about 200° C. for a period of time sufficient to effect conversion to the desired imidazoline of corresponding formula (I). Advantageously, the conversion is conducted under an inert gas atmosphere, such as under a blanket of nitrogen or like inert gas. The presence of an inert organic solvent such as mixed xylenes will also promote the desired reaction. Progress of the reaction may be followed by conventional analytical technique, such as infra-red spectroscopy to observe appearance of the C=N bond.

The carboxyamides of the formula (III) given above may be prepared by reacting together the Diels-Alder adduct of acrylic acid and α-terpinene, and a polyamine of formula (II) described above. The reaction is carried out by mixing the reactants together in equal molar proportions and heating the mixture under reflux conditions. Advantageously the reaction is carried out in the presence of an inert solvent and under an inert gas atmosphere.

The reaction is generally complete in from 1 to 30 hours. Completion of the reaction may be observed by the cessation of water of reaction being evolved.

The term "inert solvent" is used herein to mean a solvent for the reactants which does not enter into or adversely affect the desired course of the reaction. Representative of inert solvents are toluene and xylene.

Inert gases include nitrogen and argon.

At the conclusion of the reaction the desired carboxyamide product (III) may be separated from the reaction mixture by conventional technique. For example, unreacted reagent and solvent may be separated from the desired product of formula (III) by distillation.

The corrosion inhibiting compositions of the invention are prepared by the simple admixture of a metal corrosion inhibiting proportion of the above-described adducts and/or their polyamine derivatives with an oil carrier such as a petroleum oil or grease. Preferred as the oil carrier is a mineral oil. A corrosion inhibiting proportion is defined herein as that proportion which will inhibit oxidation of the metal in the presence of an oxidant such as oxygen. In general, a corrosion inhibiting proportion will comprise from about 0.1 to 2.0 percent by weight of the composition.

The following examples describe the manner and the process of making and using the invention and set forth the best mode contemplated by the inventor for carrying out the invention, but are not to be construed as limiting. Where reported, the following tests were carried out.

ANTI-CORROSION

An aliquot of the test compound was admixed with a light mineral oil (Rudol) having a viscosity within the range of 145–155 SSU at 37.8° C. The oil based compositions were then tested according to the method of ASTM test procedure D-665-A. In this test, a mixture of 300 ml of the oil under test is stirred with 30 ml of distilled water at a temperature of 60.0° C. with a cylindrical steel specimen completely immersed within. After 24 hours immersion, the appearance of the metal surface is rated. In order to report an oil as passing or failing, the test must be conducted in duplicate. An oil is reported as passing the test if both specimens are rust-free at the end of the test period. An oil is reported as failing the test if both specimens are rusted at the end of the test period. If one specimen is rusted while the other is free of rust, tests on two additional specimens are made.

PREPARATION 1

A reaction vessel fitted with a stirrer, thermometer, Dean-Stark trap and nitrogen gas inlet was charged with 280.2 g (1.347 moles) of the 1:1 acrylic acid adduct of α-terpinene, 186.9 g (1.28 moles) of triethylenetetraamine and 11 g of xylene. The charge was heated under nitrogen gas to reflux temperature, until water ceased being generated. Xylene was then removed under vacuum, leaving a residue (425 g) of yellow, very viscous liquid containing the compound of formula (III) given above, wherein n is 2.

PREPARATION 2

The procedure of Preparation 1, supra., was repeated except that the triethylenetetraamine as used therein was replaced with an equal proportion of tetraethylenepentamine to obtain a light yellow, viscous fluid which contains the amide of formula (III) given above wherein n is 3.

PREPARATION 3

The procedure of Preparation 1, supra., was repeated except that the proportion of the adduct reactant was increased to 560.4 g (2.56 moles) to obtain the dicarboxamide of formula:

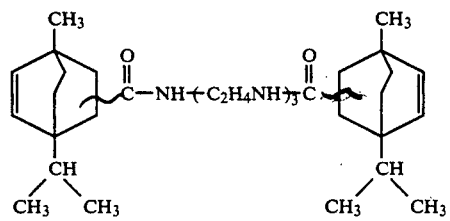

Tested for its anti-corrosion activity, this preparation was found to pass the above-described test at a concentration in mineral oil of 1.0 percent.

EXAMPLE 1

A portion of the product of Preparation 1, supra., was heated from a temperature of 185° C. to 250° C. over four hours until water removed ceased to obtain a compound of the formula (I) wherein n is 1.

EXAMPLE 2

A portion of the product of Preparation 2, supra., was heated to a temperature of 185° C. to 250° C. over six hours until water removed ceased to obtain a compound of the formula (I) wherein n is 2.

EXAMPLE 3

Aliquots of each of the imidazolines prepared in Examples 1 and 2, supra., are separately mixed with varying proportions of light mineral oil (Rudol). The mixtures so prepared were then tested for their anti-corrosion activity, in comparison to the anti-corrosion activity of the oil alone (control). The test results are shown in the Table 1, below.

TABLE 1

| ANTIRUST PERFORMANCE | | | |
|---|---|---|---|
| Additive Concentration | Additive of Example 1 | Additive of Example 2 | Control (Oil) |
| 0.0 (wgt %) | Failed | Failed | Failed |
| +0.01 | Failed | Failed | |
| +0.025 | Failed | Failed | |
| +0.05 | Passed | Passed | |
| +0.10 | Passed | Passed | |
| +0.25 | Passed | Passed | |
| +0.5 | Passed | Passed | |

What is claimed is:

1. An imidazoline of the formula:

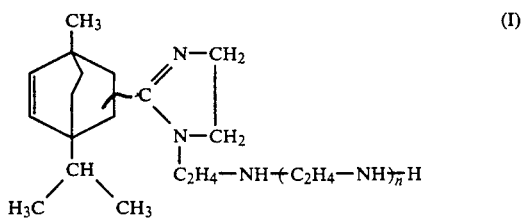

wherein n represents a whole number integer of from 1 to 6.

2. The imidazoline of claim 1 wherein n is 1.

3. The imidazoline of claim 1 wherein n is 2.

* * * * *